United States Patent [19]

Habbal

[11] 4,341,528

[45] Jul. 27, 1982

[54] SIMPLE, NON-CHROMATOGRAPHIC, HIGHLY SPECIFIC METHOD FOR THE DETERMINATION OF URINARY VANILMANDELIC ACID

[75] Inventor: M. Zouheir M. Habbal, Beirut, Lebanon

[73] Assignee: Rational Alternative, Mission Viejo, Calif.

[21] Appl. No.: 174,132

[22] Filed: Jul. 31, 1980

[51] Int. Cl.³ .................. G01N 33/52; C07C 107/06; C09B 29/00

[52] U.S. Cl. .............................. 23/230 B; 23/230 M; 23/929; 260/207

[58] Field of Search ............... 23/230 B, 230 M, 929; 260/207; 252/408

[56] References Cited

U.S. PATENT DOCUMENTS

| | | | |
|---|---|---|---|
| 3,236,601 | 2/1966 | Harvill | 23/929 X |
| 3,446,751 | 5/1969 | Weichselbaum | 23/230 B |
| 3,482,942 | 12/1969 | Schneider | 23/230 B |
| 3,585,004 | 6/1971 | Mast | 23/929 X |
| 3,836,332 | 9/1974 | James | 23/929 X |

FOREIGN PATENT DOCUMENTS 50-55381 5/1975 Japan .................. 23/230 B

OTHER PUBLICATIONS

Siddiqui et al., Chemical Abstracts, vol. 89, 1978, No. 89: 103042g.

Primary Examiner—Arnold Turk
Attorney, Agent, or Firm—Knobbe, Martens, Olson, Hubbard & Bear

[57] ABSTRACT

The Habbal reaction as a simple spectrophotometric method for the determination of urinary vanilmandelic acid (VMA) is presented. The Habbal reaction is based on the diazo reaction, the specificity of which is maximally increased by citrate buffer extraction of urinary phenolic acids and ethyl acetate extraction of the diazo derivative. The excellent specificity of the general reaction is proved by interference studies, specific destruction of VMA and chromatography. However, the diazo derivative of VMA is unstable in organic solvent ethyl acetate and, according to the Habbel reaction, is stabilized by dimethylsulfoxide (DMSO) and 2-amino-2-methyl-1-propanol (AMP) to give a stable blue chromophore absorbing maximally at 600 nm. The method is quick (20 minutes), exhibits excellent sensitivity, linearity and correlation with the highly specific method of bidirectional paper chromatography.

3 Claims, 5 Drawing Figures

SIMPLE, NON-CHROMATOGRAPHIC, HIGHLY SPECIFIC METHOD FOR THE DETERMINATION OF URINARY VANILMANDELIC ACID

The determination of urinary vanilmandelic acid (VMA), the major peripheral metabolite of catecholamines (1) has been used as a good indicator of the neural and adrenal medullary overactivity especially in the detection and the establishment of the presence of pheochromocytoma in adults (2) and neuroblastoma in children (3).

Literature abounds with analytical methods for the determination of urinary VMA. These include spectrophotometry (4,5,6), electrophoresis (7,8), paper and thin-layer chromatography (9,10), gas chromatography (11,12,13) and isotopic dilution (14). As discussed by Sandler and Ruthven in their review on VMA and homovanillic acid (HVA) methods of analysis (15), all these techniques suffer one or more of the following disadvantages: long time for analysis, non-specificity or being sophisticated enough not to warrant their use in most laboratories.

In spite of these limitations, the spectrophotometric method of Pisano (6) is widely used although it is time-consuming and lends itself to interference by normal metabolites such a p-hydroxymandelic acid, many drugs and gives results that are over 100 percent higher than results obtained by the more accurate and specific methods such as bidirectional paper chromatography (16).

Recently, a rapid colorimetric method (17) has been presented for the assay of VMA combining the determination of VMA as an azo dye after Gitlow (18) and the method of Pisano based on the conversion of VMA to vanillin. Here again, the values of VMA, although favorably compare with those of Pisano, they are still higher than values reported by the specific methods (16).

SUMMARY OF THE INVENTION

The invention constitutes an improved method for determining urinary vanilmandelic acid, using the Habbal reaction the improvement comprising extracting the diazo derivative of vanilmandelic acid into ethyl acetate, and stabilizing the extract with dimethylsulfoxide and 2-amino-2-methyl-1-propanol to give a stable chromophore which optically absorbs at 600 nm. It is the discovery of this stable chromophore and the formation thereof using the aforementioned reagents which applicant regards as his invention. Applicant's invention is not specific concentrations, amounts, etc., and nothing herein shall be read or construed to limit applicant's invention to the specific best mode described.

The present improvement is carried out using conventional spectrophotometric methods, the invention lying in the discovery that a particular chromophore can be formed, stabilized and then determined using known and established techniques.

THE BEST MODE

The following procedure is the best mode presently known for carrying out the invention. It must be absolutely understood, however, that the specific quantities, concentrations, material sources, etc., are given solely to set forth the best mode and do not in any measure or any sense limit or define the invention.

MATERIALS AND REAGENTS

For organic and inorganic compounds and solvents analytical grade reagents are used. VMA, phenol carboxylic acids and other metabolites are purchased from Sigma. Eastman-Kodak (Trademark) Silica Gel thin-layer sheets are used for chromatography. Collection of Urine: A 24 hour sample, free of drugs, is used.

A simple diet is given with no restriction on fruits, beverages or chocolate. Preservation is done by the addition of 10 ml of 6 N HCl for each sample before collection.

REAGENTS

A. Potassium carbonate, 1 M
B. Citrate buffer, 0.2 M, pH 4.0
C. P-nitroaniline, 20 mM in 1 N HCl
D. Sodium nitrite, 40 mM in water
E. P-nitrobenzenediazonium chloride, prepared just before use by mixing equal volumes of C and D. Chromatographic solvents: I. Benzene, II. Hexane-Benzene-pyridine (65:20:15), III. Benzene-Isopropanol-Acetic acid (60:40:1).

Methods

A. Determination of urinary VMA:
1. 2 ml of acidified urine is mixed with 2.0 gm of sodium chloride and extracted with 5.0 ml of ethylacetate for 2 minutes on a Vortex mixer. A second sample of urine with an internal standard of VMA (10 UL of 1 mg/ml) is run at the same time.
2. After phase separation, 4.0 ml of ethyl acetate solution is extracted with 5.0 ml of citrate buffer for 2 minutes.
3. The ethyl acetate layer is discarded and 2.0 ml of the buffer layer is mixed with 3.0 ml of potassium carbonate solution. 20 U1 of fresh diazonium reagent is added and the diazonium salt of VMA is extracted with 3.0 ml of ethyl acetate after 2 minutes by shaking for 30 seconds.
4. 2.0 ml of the ethyl acetate extract is mixed with 1.0 ml of dimethylsulfoxide and 0.05 ml of 2-amino-2-methyl-1-propanol.
5. The resulting blue color is measured spectrophotometrically at 600 nm using water to zero the machine. The sample with the internal standard is used for calculation. Creatinine is done by the Autoanalyzer II technique.

B. Determination of interference by urinary metabolites: 25 Ul of 0.01 M of the metabolite is added to 2.0 ml of citric buffer followed by 3.0 ml of potassium carbonate solution. The following steps are similar to those in A (steps 3,4,5).

C. Thin-layer chromatography: This is done by the ascending technique. When the solvent front travels to about 1 cm from the upper edge of the sheet, it is air-dried and examined by visual inspection of the colored diazo derivative.

D. Bidirectional paper chromatography: This is done after the method of Armstrong et al. (1).

E. Spectrophotometric studies and measurements are done with Varian Spectrophotometer Series 634 equipped with Varian 9176 Model Recorder.

Results

Figure 1:
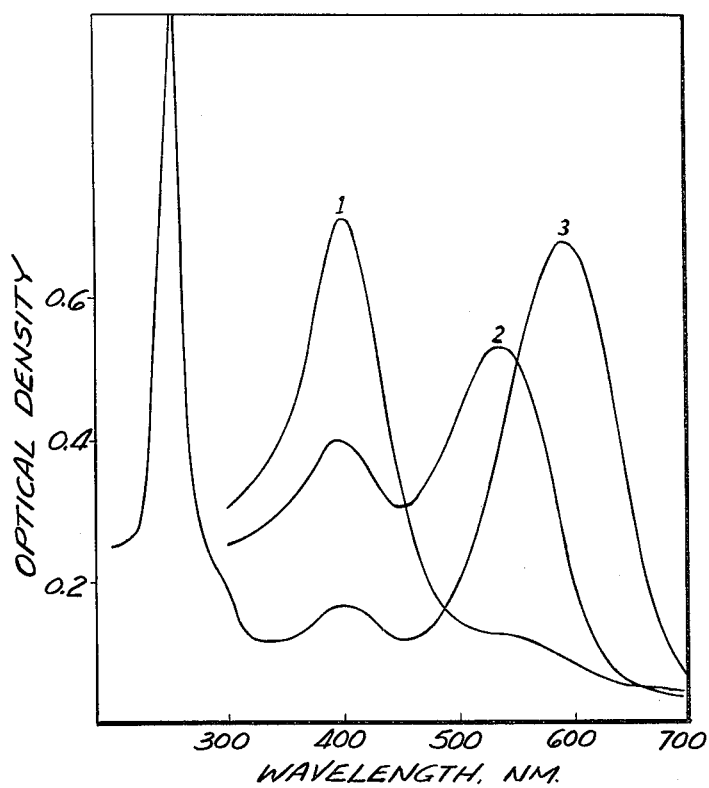
FIG. 1 is the absorption spectrum of the diazo derivative of VMA in various solvents. (1) ethyl acetate, (2) ethyl acetate+isopropanol, (3) ethyl acetate+dimethylsulfoxide+2-amino-2-methyl-1-propanol.

1. Stability of the diazo derivative of VMA:

When a pure sample of VMA is added to citrate buffer and processed as mentioned under Methods, a pink color is extracted with the organic ethyl acetate which fades slowly to a yellow color. As seen in FIG. 1, the latter has a maximum at 400 nm of the many attempts used to stabilize the color, isopropyl alcohol offered some protection. However, addition of dimethylsulfoxide and a trace of 2-amino-2-methyl-1-propanol produces a very stable blue chromophore absorbing at a maximum of 600 nm. Of the various reagents tested (KOH, NaOH, $NH_3$, diethylamine (DEA), triethylamine (TEA), and 2-amino-2-methyl-1-propanol, only 2-amino-2-methyl-1-propanol gives the stable blue color with maximum absorbance. Maximum color development is achieved with 1 M $K_2CO_3$. Ammonium hydroxide (1 N) gives a similar result. The use of 1 N NaOH destroys the formation of the diazo derivative of VMA.

Figure 2:
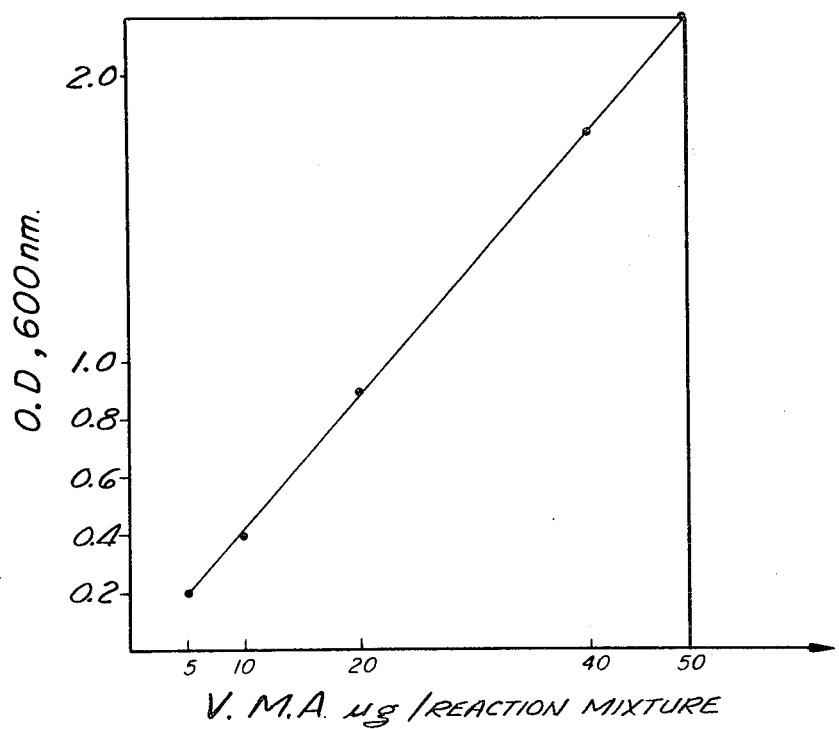
FIG. 2 is the calibration curve for the determination of VMA by the present method.

2. Sensitivity and linearity of the method:

As it is seen in FIG. 2, the present reaction is linear up to 50 Ug of VMA. A concentration of 5 Ug/ml of citrate buffer gives an absorbance of 0.1 at 600 nm. The abosrbance of the diazo reaction extracted with butanol and measured at 540 nm is half that when compared with our method.

Figure 3:
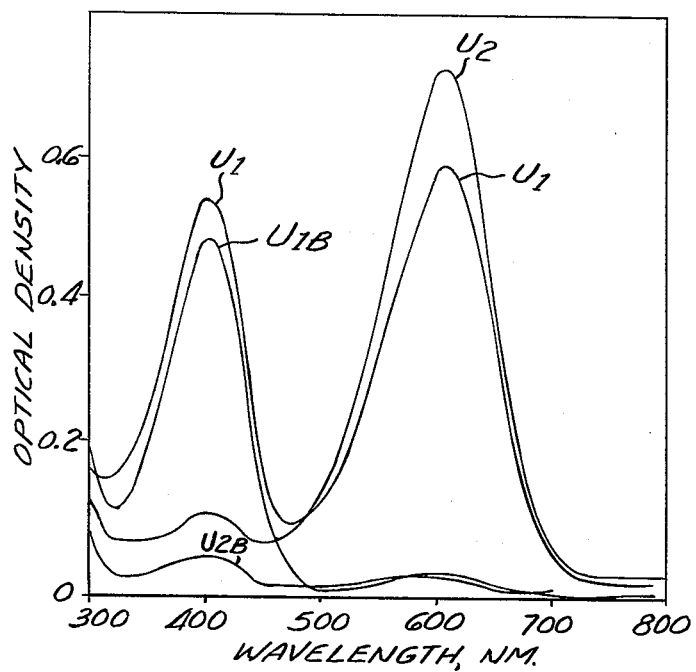
FIG. 3 depicts the effect of the diazonium salt concentration on the absorption spectrum of diazo VMA. (U1)—Urine sample+200 U1 of the diazo reagent, (U2)—The same urine sample+20 U1 of the diazo reagent. U1B,U2B are the same as above except that the components of the diazo reagent are added successively to the reaction mixture.

3. Concentration of the diazonium salt:

Using increasing volumes of the diazo reagent with the same amount of VMA shift the color of the final reaction from blue to green. This is evident in FIG. 3 where 10 times concentration of the diazo reagent produces no extra absorbance at 600 nm, but a significant peak at 400 nm. The concentration of the diazo reagent suggested before is enough to react with 15 Ug of VMA/ml of urine.

4. Analytical recoveries: These are shown in Table 1 where various amounts of standards are added to a urine sample. They range from 92% to 110% (average: 98.6%).

TABLE 1

| | Analytical Recovery of Added VMA | | |
|---|---|---|---|
| Added VMA | Estimated Concen. Ug/mg creatinine | Observed Concen. | Recovery % |
| 0 | — | 5.0 | — |
| 5 | 10 | 9.2 | 92 |
| 10 | 15 | 16.0 | 106 |
| 15 | 20 | 18.5 | 92 |
| 20 | 25 | 27.5 | 110 |
| 25 | 30 | 28.0 | 93 |

5. Specificity of the method:

A. Interference studies:

These are done by comparing the intensity of the colors produced by various urinary metabolites with that of VMA at equimolar concentrations. It is evident from Table 2 that only metanephrine, nor metanephrine, and 3-methoxy 4-hydroxyphenyl glycol produce significant interference.

TABLE 2

| Urinary Metabolites Evaluated For Interference | |
|---|---|
| Compound | % absorption relative to VMA (100) |
| Vanilmandelic acid | 100.0 |
| B-phenyl pyruvic acid | 3.3 |
| p-hydroxy phenyl acetic acid | 0.0 |
| Homovanillic acid | 0.0 |
| Gentisic acid | 0.0 |
| Pipecolic acid | 0 |
| Resorcinol | 10.0 |
| P-hydroxymandelic acid | 0 |
| Kynurenic acid | 0 |
| Xanthurenic acid | 0 |
| Pyrocatechol | 0 |
| 5-Hydroxyindole acetic acid | 0 |
| 4-hydroxy 3-methoxy phenyl lactic acid | 0 |
| Homo gentisic acid | 0 |
| Indole 3-acetic acid | 0 |
| 4-hydroxy 3-methoxy phenyl pyruvic acid | 0 |
| 4-hydroxy phenyl pyruvic acid | 0 |
| Vanillin | 0 |
| Normetanephrine | 120 |
| Metanephrine | 120 |
| HMPG | 90 |
| Vanillic acid | 26 |
| Anthranillic acid | 0 |
| p-hydroxy benzoic acid | 0 |
| Kynurenine | 0 |
| B-Indole acrylic acid | 5.0 |
| 3,4 dihtdroxy phenyl acetic acid | 0 |
| Caffeic acid | 0 |
| Ferulic acid | 8.0 |
| 3-Methoxy tyramine | 5.0 |
| 3,4 dihydroxy mandelic acid | 5.0 |
| 3-Methoxy tyrosine | 0 |
| L-DOPA | 0 |
| 3-Indole lactic acid | 0 |
| Indole-3 acetic acid | 0 |

Figure 4:
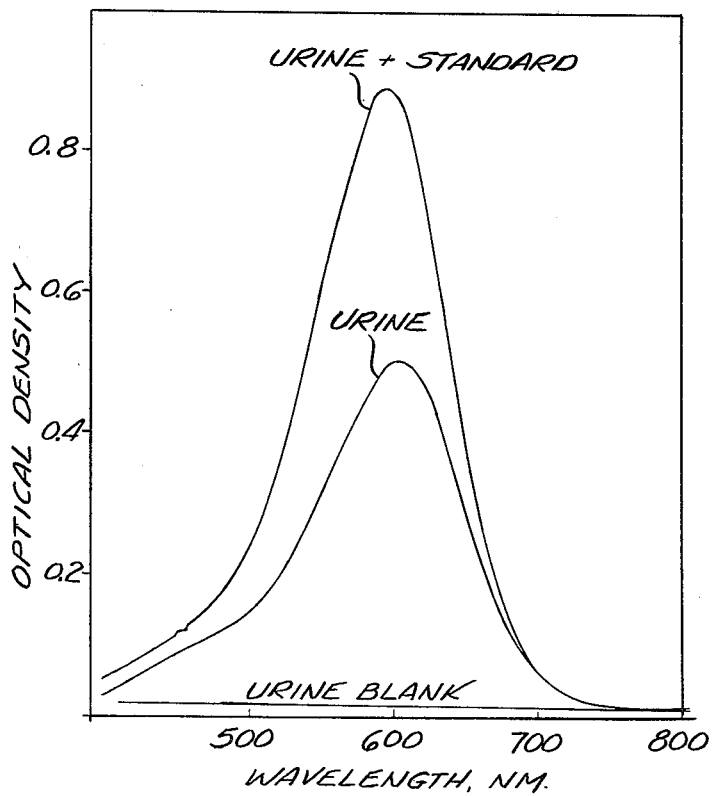
FIG. 4 is the absorption spectrum of urinary VMA measured by our method (urine) and following periodate treatment (blank). The sample with the internal standard is plotted to confirm the authenticity of urinary VMA.

B. Assay of urinary VMA following its destruction by periodate:

Since vanillin produces no color (see Table 1), oxidation of VMA to vanillin by periodate before the addition of the diazo reagent should produce no color in the final analysis. This is shown in FIG. 4 where such treated urine showed no absorbance at 600 nm as in urine blank.

C. Thin-layer chromatographic studies:

These studies are done on the ethyl acetate extract containing the diazo-reactive compound(s) of urine. One spot is seen in all three types of solvents having an $R_f$ value of 0.17 in solvent I, 0.27 in solvent II, 0.74 in solvent III, all of which coincide with an authentic sample of VMA.

6. Statistical analysis of the results:

Statistical analysis of the results obtained by our method in comparison with those from the method of Pisano (6) and of the method of Armstrong et al. (1) is shown in Table 3.

TABLE 3

Statistical Analysis of Results Obtained By The Present Method (Y) And Other Methods (X)

|  | Pisano | Armstrong |
|---|---|---|
| Regression line | Y = 0.480 + 0.048 | Y = 1.10X − 0.305 |
| Coefficient of determination | 0.673 | 0.987 |
| No. of determinations | 16 | 16 |

Figure 5:
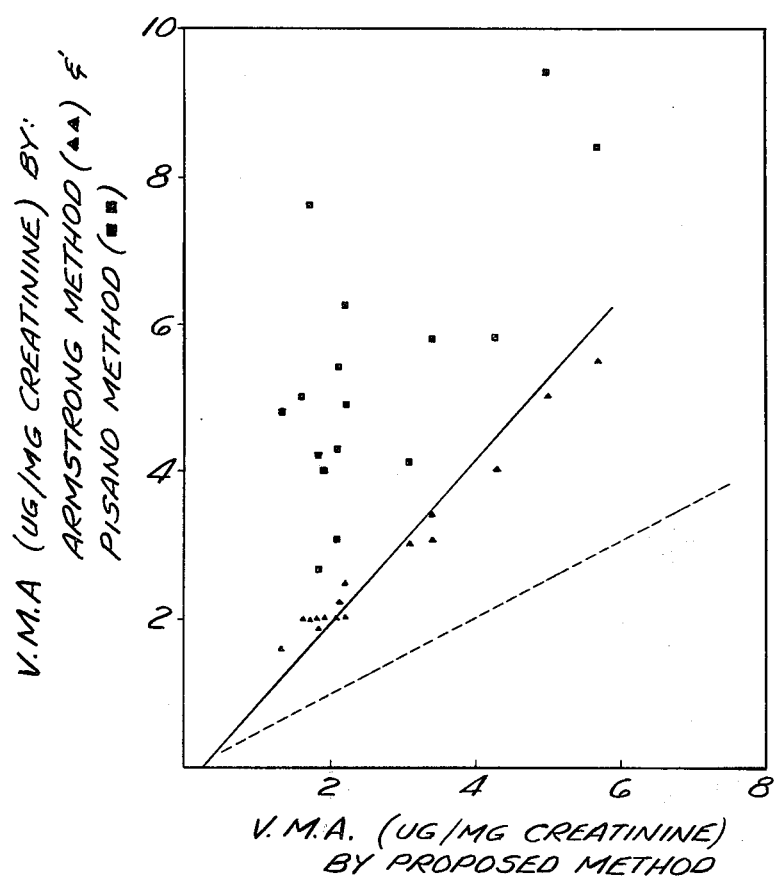
FIG. 5 depicts the correlation between urinary VMA results by the present method and those of Armstrong and Pisano.

Good agreement and correlation is demonstrated between our method and that of Armstrong, but there is a significant difference between our results and those of Pisano. FIG. 5 demonstrates the correlation between our method and both procedures.

Discussion

The determination of VMA by the diazo method, although quick, is non-specific (18). The specificity of the present method has resulted from the interplay of two factors: the extraction of ethyl acetate layer with citrate buffer instead of sodium or potassium carbonate, and the extraction of the diazo derivative of VMA by ethyl acetate instead of butanol as suggested by the non-specific procedure. In fact, I have detected less acids by extraction with citrate buffer than with carbonate solution as has been shown by Gumboldt (17). However, the greater part of specificity is due to specific stability of diazo VMA by the dimethylsulfoxide which is supported by thin-layer chromatographic studies. The interference by metanephrins is negligible since they are not extracted with ethyl acetate from acidified urine and so the case for MHPG which is extracted normally as a water-soluble sulfate ester (19). The interfering effect of vanillic acid is also eliminated since it is not extracted with citrate buffer from ethyl acetate. Therefore, these specificity studies have proved no interference from endogenous sources. But, one is still faced with interference from an endogenous source which is the diazo reagent itself. It is evident from FIG. 3 where increasing the amount of that reagent adds no extra absorbance at 600 nm—but a significant increase at 400 nm. The latter peak is most probably due to p-nitrophenol, a degradation product of the reagent, although it can be argued that being a relatively strong acid, it should not be extracted with the ethyl acetate from alkali solutions. Therefore, in a normal urine with low value of VMA, a high concentration of the diazo reagent will falsely raise that value up to a level comparable with that of Pisano.

The concentration proposed by this method is enough to react with 15 Ug of VMA/ml. urine which is rarely exceeded and can be increased proportionately when necessary.

The high specificity of this present method is reflected by the values obtained when compared with other methods. This is evident from the correlation study done with Armstrong procedure. The latter is well known to correlate with the isotopic dilution method (14).

It is to be emphasized that the specific best mode disclosed does not in any way or any degree limit or suggest any limitation of the invention to the concentrations, ratios, amounts, etc. of the reagents. Those competent in analytical techniques will recognize that there is enormous variation possible in such variables as overall amount, concentration, etc. For example, it is generally accepted that a component to be determined should be extracted into the smallest amount of extract solvent which will give a good partition of the component, provide convenient volumes for handling, and not overly dilute the extracted component, but absolute values, fixed maxima and minima rarely if ever have any place in such techniques. Likewise, it is usually regarded as optimum to provide sufficient excess of a reagent to assure complete reaction of the component to be determined, but not such a great excess as would interfere with quantitative measurements. In many instances, a very large excess is used to give a constant background measurement for reagent contribution to the measurement. Thus, the precise values in amounts, volumes, concentrations, ratios, etc. are simply the best mode arrived at by the inventor and do not represent, in any sense, the inventive concept and nothing herein shall be so construed. Without attempting any definite limitations, and base upon predictions from experience with the reagents and chromophore involved and competence in the technical field in which this invention lies, it is projected that the ratio of ethyl acetate extract of the diazo derivative of vanilmandelic acid to other stabilizing reagents will generally be in the range of from about 0.1 to about 0.9 parts of dimethylsulfoxide and 0.01 to 0.5 part, and usually from 0.01 to 0.1 part, of 2-amino-2-methyl-1-propanol per part of such extract, all by volume. But, as discussed, these are general ranges and not critical to the invention nor do these ranges constitute the invention, the discovery or any essential part thereof.

Industrial Application

This invention finds practical and industrial application in hospitals and clinics generally throughout the world where diagnostic tests are performed.

References

1. Armstrong, M. D., McMillan, A. and K, N. F. Shaw (1957). Biochim. Biophys. Acta. 25, 422–423.
2. Swerdloff, R. S. (1972). Cal. Med. 117, 44–49.
3. Von Studnitz, W., Kaser, H., Sjoerdsma, A. (1963) New Eng. J. Med. 269, 232–235.
4. Sandler, M., Ruthven, C. R. J. (1959). Lancet ii, 1034.
5. Sandler, M., Ruthven, C. R. J. (1961). Biochem. J. 80, 78–82.
6. Pisano, J. J., Crout, J. R., Abraham, D. (1962). Clin. Chim. Acta 7, 285–291.
7. Klein, D., Chernaik, J. M. (1961). Clin. Chem. 7, 257–264.
8. Eichhorn, F., Rutenberg, A. (1963). Clin. Chem. 9, 615–619.
9. Armstrong, M. D., Shaw, K. N. F., Wall, P. E. (1956). J. Biol. Chem. 218, 293–303.
10. Annino, J. S., Lipson, M., Williams, L. A. (1965). Clin. Chem. 11, 905–913.
11. Sprinkle, T. J., Porter, A. H., Gr-et, M. Williams, C.,. (1969). Clin. Chim. Acta 25, 409–411.
12. Kahane, Z., Mowat, J. H., Vestergaard, P. (1969). Clin. Chim. Acta 26, 307–311.
13. Angaard, E., Sedrall, G. (1969). Anal. Chem. 41, 1250–1256.
14. Weise, V., K., Mcdonald, R. K., Labrosse, E. H. (1961). Clin. Chim. Acta 6, 79–86.

15. Sandler, M., Ruthven, C. R. J. (1966). Pharm. Rev. 18, 343-351.

16. Gittow, S. E., Mendlowitz, M., Wilk, E. K., Wilk, S., Wolf, R. L., Bertani, L. M. (1968). J. Lab. Clin. Med. 72, 612-620.

17. Gumboldt, G. (1977). Clin. Chem. 23, 1949-1950.

18. Gitlow, E. S., Bertani, L., M., Rausen A., (1970). Cancer, 25, 1377-1383.

19. Bigelow, L. B., Neal, S, Weil-Malherbe, M. (1971). J. Lab. Clin. Med. 77, 677-683.

What is claimed is:

1. The method for the determination of vanilmandelic acid comprising the steps of:
   (a) forming a diazo derivative by reacting a p-nitrobenzenediazonium salt with vanilmandelic acid;
   (b) extracting said derivative into ethyl acetate;
   (c) forming a stable chromophore of said derivative by adding to the ethyl acetate extract thereof effective amounts of dimethylsulfoxide and 2-amino-2-methyl-1-propanol; and
   (d) quantitatively determining said chromophore.

2. The method of claim 1 wherein step (d) comprises determining the chromophore spectrophoto metrically.

3. The Habbal Reaction comprising forming a stable chromophore of a diazo derivative by reacting a p-nitrobenzenediazonium salt with vanilmandelic acid, extracting the resulting derivative into ethyl acetate and adding to said ethyl acetate extract effective amounts of dimethylsulfoxide and 2-amino-2-methyl-1-propanol.

* * * * *